US006749715B2

(12) United States Patent
Gilton et al.

(10) Patent No.: US 6,749,715 B2
(45) Date of Patent: Jun. 15, 2004

(54) SYSTEM AND METHOD FOR ANALYZING A SEMICONDUCTOR SURFACE

(75) Inventors: Terry L. Gilton, Boise, ID (US); Troy R. Sorensen, Boise, ID (US)

(73) Assignee: Micron Technology, Inc., Boise, ID (US)

(*) Notice: Subject to any disclaimer, the term of this patent is extended or adjusted under 35 U.S.C. 154(b) by 246 days.

(21) Appl. No.: 09/864,605

(22) Filed: May 24, 2001

(65) Prior Publication Data

US 2001/0023130 A1 Sep. 20, 2001

Related U.S. Application Data

(62) Division of application No. 09/386,124, filed on Aug. 30, 1999, now Pat. No. 6,420,275.

(51) Int. Cl.$^7$ .................................................. C23F 1/00
(52) U.S. Cl. ................... 156/345.13; 134/1.3; 356/316; 356/237.2; 250/258
(58) Field of Search .................... 156/345.13, 345.1; 216/84; 134/1.3; 356/316, 237.2, 237.3, 237.4; 250/258

(56) References Cited

U.S. PATENT DOCUMENTS

| | | | |
|---|---|---|---|
| 4,104,026 A | | 8/1978 | Brooker et al. |
| 4,894,529 A | | 1/1990 | Borden et al. |
| 4,920,071 A | | 4/1990 | Thomas |
| 4,926,021 A | | 5/1990 | Streusand et al. |
| 4,990,459 A | | 2/1991 | Maeda et al. |
| 5,129,991 A | | 7/1992 | Gilton |
| 5,151,168 A | | 9/1992 | Gilton et al. |
| 5,188,723 A | | 2/1993 | Yu et al. |
| 5,232,749 A | | 8/1993 | Gilton |
| 5,248,614 A | | 9/1993 | Wang |
| 5,259,254 A | * | 11/1993 | Zhu et al. ................ 73/864.81 |
| 5,271,798 A | * | 12/1993 | Sandhu et al. ............. 438/745 |
| 5,315,369 A | | 5/1994 | Zadgorska et al. |
| 5,325,730 A | | 7/1994 | Wang |
| 5,364,803 A | | 11/1994 | Lur et al. |
| 5,367,163 A | | 11/1994 | Otsuka et al. |
| 5,400,665 A | | 3/1995 | Zhu et al. |
| 5,441,904 A | | 8/1995 | Kim et al. |
| 5,445,994 A | | 8/1995 | Gilton |
| 5,501,767 A | | 3/1996 | Sorensen et al. |
| 5,597,444 A | | 1/1997 | Gilton |
| 5,633,172 A | * | 5/1997 | Shimazaki ................ 436/177 |
| 5,668,394 A | | 9/1997 | Lur et al. |
| 5,691,211 A | | 11/1997 | Sorensen et al. |
| 5,783,938 A | * | 7/1998 | Munson et al. ............ 324/71.2 |
| 5,837,598 A | | 11/1998 | Aronowitz et al. |
| 5,851,680 A | | 12/1998 | Heau |
| 5,853,492 A | | 12/1998 | Cathey et al. |
| 6,010,637 A | * | 1/2000 | Lee et al. ................... 216/96 |
| 6,261,845 B1 | * | 7/2001 | Verhaverbeke et al. ...... 436/55 |
| 6,265,717 B1 | * | 7/2001 | Sakata et al. .............. 250/289 |
| 6,420,275 B1 | * | 7/2002 | Gilton et al. .............. 438/745 |
| 6,429,935 B1 | * | 8/2002 | Duan ....................... 356/316 |
| 6,519,031 B2 | * | 2/2003 | Gilton et al. .............. 356/316 |

OTHER PUBLICATIONS

Merriam–Webster's Dictionary "peristaltic pump" "gas chromatography" . pp. 865 and 481 respectively. (1999).*

* cited by examiner

Primary Examiner—Gregory Mills
Assistant Examiner—Sylvia R. MacArthur
(74) Attorney, Agent, or Firm—Knobbe, Martens, Olson & Bear, LLP

(57) ABSTRACT

A method and apparatus for analyzing a semiconductor surface obtains a sample from a localized section of a wafer. The sample is obtained by isolating a section of a wafer with a sampling apparatus, dispensing liquid onto the isolated section of the wafer, dissolving compounds of interest in the liquid, removing a portion of the liquid, and analyzing the liquid and dissolved compounds of interest. The liquid can be an etching solution, an organic solvent, or other suitable solvent. Samples and analyses can, thus, be obtained as a function of position on the wafer. Analyses as a function of depth can also be determined by sampling and analyzing an isolated portion of the wafer as a function of time.

27 Claims, 4 Drawing Sheets

SYSTEM AND METHOD FOR ANALYZING A SEMICONDUCTOR SURFACE

This application is divisional of U.S. patent application Ser. No. 09/386,124, filed on Aug. 30, 1999, now U.S. Pat. No. 6,420,275, the entirety of which is hereby incorporated herein by reference.

BACKGROUND OF THE INVENTION

1. Field of the Invention

This invention relates to analyzing a semiconductor surface. In particular, the invention relates to analyzing an isolated area on a wafer surface.

2. Background

There are many methods for obtaining samples from the surfaces of wafers for determination of surface contamination and bulk analysis. One common technique for determining surface contamination is vapor phase deposition (VPD). In this method, an etchant such as hydrofluoric acid is vaporized, and the surface of the wafer is exposed to the vapor. The etchant vapor forms a fog on the surface.

A droplet of deionized water with a low concentration of hydrofluoric acid and optionally hydrogen peroxide is then placed on the surface of the wafer, and a robot tilts the wafer so that the droplet rolls across the surface, gathering up the etchant fog with the dissolved contaminants. The droplet and dissolved contaminants are analyzed by appropriate analytical methods such as with a spectrometer. The concentration of contaminants per unit surface area of wafer is calculated as the total quantity of contaminant in the droplet divided by the total surface area of the wafer. This sampling method therefore cannot be used to obtain spatial information on the contaminant levels as a function of position on the wafer. Rather, the total contaminant level on the entire surface is obtained.

Bulk analyses of the composition of wafers have also been obtained by dipping the wafer into an etchant to dissolve a portion of the wafer and analyzing the constituents in the etchant. The wafer is weighed before and after dipping in the etchant solution to determine how much of the wafer dissolved. The bulk analysis is assumed to be the weight of each constituent in the etchant solution divided by the weight of the wafer which dissolved. The bulk analysis by this technique is often imprecise. Further, the composition of the wafer as a function of the position on the wafer cannot be determined by this sampling method.

It is possible to etch a wafer as a function of position as disclosed by U.S. Pat. No. 5,271,798. However such an approach does not appear to analyze the wafer composition as a function of position.

SUMMARY OF THE INVENTION

The invention obtains a sample from a localized section of a wafer. A sampling apparatus isolates a section of the wafer and then dispenses liquid onto the isolated section. After the liquid has dissolved elements of interest in or on the wafer, a sample of the liquid is transferred to an analyzer. The liquid can be an etching solution, an organic solvent, or other suitable solvent. An analysis of the wafer can thus be obtained as a function of position on the wafer. Furthermore, an analysis of the materials located at different depths within the wafer can be obtained.

One embodiment of the invention relates to a method for sampling and analyzing a selected portion of a semiconductor wafer. The method comprises isolating a portion of a wafer, and dispensing a liquid onto the isolated portion of the wafer. The method also comprises removing at least a portion of the liquid and analyzing the liquid.

Another embodiment of the invention relates to a method for selectively analyzing a wafer surface. The method comprises obtaining a sample from an isolated portion of a wafer and analyzing the sample. An additional embodiment of the invention relates to a method for evaluating a selected section of a wafer. The method comprises dispensing a liquid onto a selected section of a wafer and pumping or moving a portion of the liquid from the selected section of the wafer.

Another embodiment of the invention relates to a method for analyzing a material selectively removed from a portion of a wafer. The method comprises forming a seal between a portion of a sampling apparatus and a portion of a wafer, thereby isolating a portion of the wafer. The method also comprises dispensing a liquid onto the isolated portion of the wafer, and removing part of the liquid from the isolated area to form a sample. The method further comprises analyzing the sample.

An additional embodiment relates to a method for evaluating an isolated section of a wafer. The method comprises dispensing an etchant onto an isolated section of a wafer and transferring a portion of the etchant from the isolated section of the wafer. The method also comprises analyzing the etchant as a function of time.

One aspect of the invention relates to a sampling apparatus for selectively evaluating portions of a wafer. The apparatus comprises a first tube that is configured to isolate a portion of a wafer. The apparatus also comprises a second tube that is configured to dispense a liquid onto the isolated portion of the wafer. The apparatus further comprises transfer tubing that is configured to transfer a portion of the liquid to an analyzer.

Another aspect of the invention relates to a test system that evaluates isolated portions of a semiconductor wafer. The test system comprises a sampling apparatus that is configured to dispense a liquid onto an isolated section of a wafer. The sampling apparatus comprises an outer tube that forms a seal between the outer tube and the isolated section of the wafer. The sampling apparatus also comprises an inner tube within the outer tube. The inner tube is configured to dispense a liquid within the isolated section of the wafer.

The testing system also comprises transfer tubing comprising a first end and a second end. The first end is connected to the outer tube of the sampling apparatus and the second end is connected to an analysis system. The transfer tubing further comprises a flexible outer surface wherein the transfer tubing is configured to transfer a portion of the liquid from the sampling apparatus to an analysis system.

The testing system further comprises a peristaltic pump or other pumping or liquid transfer system in communication with a portion of the flexible outer surface of the transfer tubing. The peristaltic pump is configured to direct the liquid in the transfer tubing to the analysis system.

Another embodiment of the invention relates to a semiconductor testing apparatus. The semiconductor testing apparatus comprises a sampling apparatus that is configured to dispense a liquid onto an isolated section of a wafer. The semiconductor testing apparatus further comprises transfer tubing that is in communication with the sampling apparatus. The transfer tubing is configured to transfer a portion of the liquid from the sampling apparatus. The semiconductor testing apparatus also comprises a peristaltic pump or other pumping or liquid transfer system that is in communication with the transfer tubing. The peristaltic pump is configured to direct the liquid in the transfer tubing to an analyzer.

An additional embodiment of the invention relates to a semiconductor testing apparatus. The semiconductor testing apparatus comprises a first means for isolating a portion of a wafer. The first means also dispenses a liquid onto the isolated portion of the wafer. The semiconductor testing apparatus further comprises a second means in communication with the first means. The second means transfers a portion of the liquid to an analysis system. The semiconductor testing apparatus also comprises a third means for transferring the liquid through the second means.

For the purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

DETAILED DESCRIPTION OF THE PREFERRED EMBODIMENT

While illustrated in the context of obtaining and analyzing a sample of a wafer as a function of position, the skilled artisan will find application for the embodiments disclosed herein in a wide variety of contexts. For example, the disclosed embodiments have utility in sampling and analyzing a wide range of solid materials in addition to wafers, as will become apparent through the examples disclosed herein.

Figure 1:
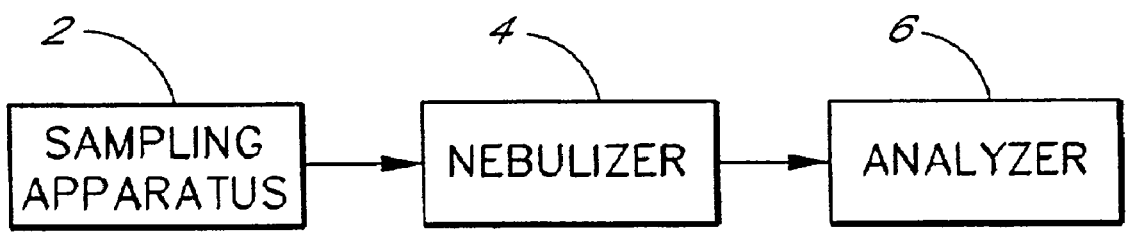
FIG. 1 is a block diagram of the major aspects of one embodiment of the invention.

FIG. 1 illustrates a block diagram of an embodiment of the invention. A sampling apparatus 2 obtains a sample from the surface of a wafer (not shown). The manner of obtaining the sample is an aspect of the invention and will be described in further detail below. The sample is then transferred to a nebulizer 4 for processing prior to analyzing in an analyzer 6. The manner of transferring the sample to the nebulizer 4 is another aspect of the invention and will be described in further detail below.

Figure 2:
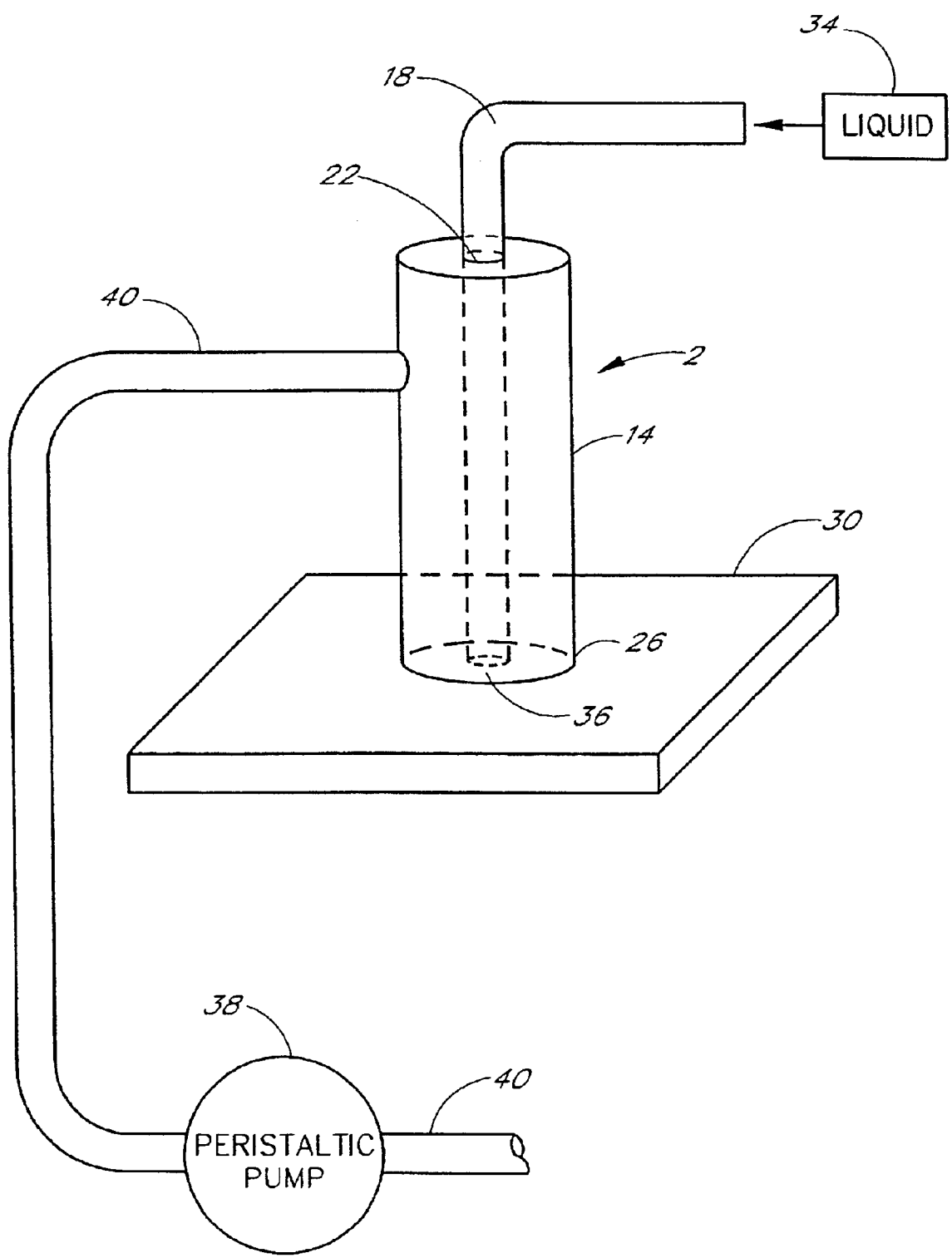
FIG. 2 is a schematic drawing of an apparatus for obtaining a sample according to one embodiment of the invention.

FIG. 2 shows an apparatus for obtaining a sample with one embodiment of the invention. The sampling apparatus 2 obtains a sample from a wafer 30. The sampling apparatus 2 comprises an outer tube 14 and a concentric inner tube 18. The concentric inner tube 18 is sealed to the outer tube 14 with a top seal 22. The bottom ends of the outer and inner tubes 14 and 18 are open. A base 26 of the sampling apparatus 2 is placed into contact with a wafer 30 so that the base 26 forms a seal with the wafer 30.

Although the invention is described with a wafer 30 as an example of a solid to be sampled, the invention is applicable to any soluble solid, any solid with a soluble component, or any solid comprising a soluble contaminant.

A liquid 34 is introduced into the inner tube 18. The liquid 34 travels through the inner tube 18 and contacts a wafer surface 36 below the end of the inner tube 18. After the liquid 34 contacts the wafer surface 36, it dissolves inorganic and/or organic materials on the wafer surface 36, a portion of the wafer 30, or both, depending on the liquid 34 which is used. The liquid 34 is chosen so that the compounds of interest dissolve in the liquid 34.

Because the base 26 forms a seal with the wafer 30, only the portion of the wafer 30 which is covered by the inside diameter of the outer tube 14 is accessible to the liquid 34. Therefore, a portion of the wafer 30 or contaminants within the perimeter of the outer tube 14 can dissolve in the liquid 34 to form a sample. The portion of the wafer 30 covered by the inside diameter of the outer tube 14 is isolated from the remainder of the wafer 30 by the seal formed between the base 26 and the wafer 30. Such sampling allows a localized sample to be obtained, rather than obtaining a single sample from the entire surface of the wafer 30.

An outlet tube 40 is attached to the outer tube 14. Although the outlet tube 40 is normally attached to the side of the outer tube 14, as shown, for example, in FIG. 2, other configurations are possible. The outlet tube 40 leads to a transport system 38. The liquid 34 is removed from the wafer surface 36 through the outlet tube 40 by the transport system 38.

Figure 3:
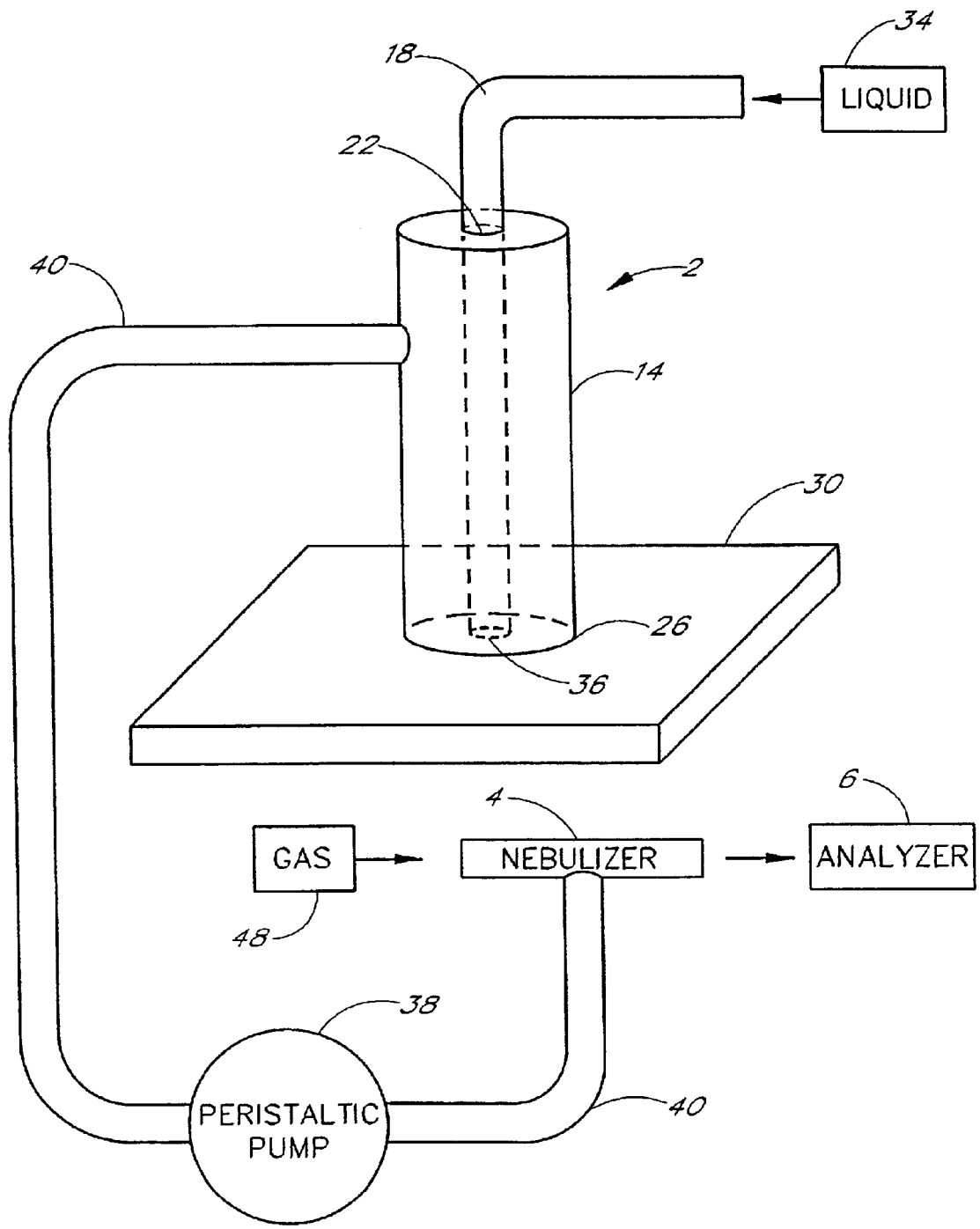
FIG. 3 is a schematic drawing showing additional embodiments of the apparatus of FIG. 2 including a method of analyzing the sample.

FIG. 3 illustrates one embodiment of the invention, where the liquid 34 which was removed from the wafer surface 36 by the transport system continues through the outlet tube 40 to the nebulizer 4, where it is mixed with a gas 48 and is analyzed by the analyzer 6.

The liquid 34 may be an inorganic solvent such as water, an organic solvent, a chemical etchant, or other suitable liquid. The liquid 34 is chosen to dissolve the materials or compounds of interest. Various embodiments of the invention and the types of liquids 34 which are suitable for use in the invention are described below. Other embodiments will be clear to one skilled in the art, and the invention is not meant to be limited to the embodiments discussed below.

In one embodiment, the liquid 34 is an etching solution that dissolves a portion of the wafer 30. If the contaminants on the surface of the wafer 30 or in the portion of the wafer 30 are soluble in the etching solution, the contaminants also dissolve. Analyzing the liquid 34 therefore provides an analysis of the dissolved portion of the wafer 30 and any dissolved impurities.

In another embodiment, the liquid 34 is an organic solvent. When an organic solvent is used as the liquid 34, organic compounds on the surface of the wafer 30 dissolve in the organic solvent. Analyzing the organic solution comprising the organic solvent and dissolved organic compounds in the analyzer 6 provides an analysis of the organic compounds on the surface of the wafer 30 or the organic solid wafer 30 in the isolated portion of the wafer 30.

In another embodiment, the liquid 34 of the invention is an etching solution comprising aqueous hydrofluoric acid. In another embodiment, the etching solution further comprises aqueous hydrogen peroxide. In one embodiment, the etching solution comprises $H_2O:HF:H_2O_2$ in a weight ratio of between 99.6:0.1:0.3 and 96.0:1.0:3.0. An exemplary etching solution comprises $H_2O:HF:H_2O_2$ in a weight ratio of 100:1:1.

The exemplary etching solution has been found to dissolve a wider range of materials than the prior art etching solutions and can therefore be used to obtain a more complete analysis of a material and impurities in the material than previous etching solutions. For example, when doing bulk analysis of a bare wafer 30, the $H_2O:HF:H_2O_2$ etching solution dissolves both the wafer 30 and hard-to-analyze impurities such as copper metal. The hydrogen peroxide in the etching solution oxidizes the copper so that it is soluble in the solution to be analyzed.

The materials of construction of the sampling apparatus 2 may vary, depending on the liquid 34. For example, if the liquid 34 is an etching solution, especially an etching solution containing hydrofluoric acid, the inner tube 18 and outer tube 14 of the sampling apparatus 2 are made of an inert material such as polytetrafluoroethylene (PTFE), sold under the tradename TEFLON®. The skilled artisan, however, will realize that a wide range of materials such as Pertourar Alkoxy (PFA) tubing, TYGON® tubing and the like may be used.

The diameters of the inner tube 18 and the outer tube 14 can vary, depending on the application. When obtaining spatial information over the surface of the wafer 30, it is desirable that the inner tube 18 be small, so that the portion of the wafer surface 36 which is exposed to the liquid 34 is small. In one embodiment of the sampling apparatus 2, the inner tube 18 has an inner diameter of 150 $\mu$m, the outer tube 14 has an inner diameter of 2 mm, and the wall thickness of the outer tube 14 is about 2 mm.

There is a balance in choosing the size of the outer tube 14. For example, if a small outer tube 14 is chosen, the sensitivity of the method decreases, because the area of the wafer 30 which is sampled is small, thus forming a small sample for analysis in the analyzer 6. However, a smaller outer tube 14 gives better spatial resolution across the surface of the wafer 30.

In one embodiment, the outlet tube 40 is made of an inert material such as TEFLON® or TYGON®. If the outlet tube 40 is made of an inert material, the liquid 34 and the materials dissolved in the liquid 34 are unlikely to change in composition during the pumping process. The sample which is analyzed in the analyzer 6 is therefore likely to be representative of the sample which was obtained from the isolated section of the wafer 30.

The transport system 38 which withdraws the liquid 34 from the wafer surface 36 can be a pump, for example a liquid pump or a vacuum pump. If the transport system 38 is a liquid pump, the liquid 34 builds up inside the outer tube 14 until it overflows into the outlet tube 40. The liquid 34 which overflows into the outlet tube 40 is pumped by the transport system 38 including the liquid pump into the nebulizer 4, where the liquid 34 is mixed with the gas 48 before being analyzed in the analyzer 6.

Peristaltic pumps are exemplary liquid pumps. Peristaltic pumps operate by squeezing the outlet tube 40 with rollers, thereby pushing the liquid 34 through the outlet tube 40. The outlet tube 40 can therefore be made of a flexible material such as a flexible plastic, when a peristaltic pump is used as the transport system 38. In another embodiment, the outlet tube 40 is connected to a flexible tube. When a peristaltic pump is used as the transport system 38, the liquid 34 remains within the outlet tube 40 until the liquid 34 enters the nebulizer 4. Thus, the liquid 34 does not contact materials such as rubber or reactive metals which could either absorb or react with the liquid 34 or the dissolved components in the liquid 34. Use of an inert material for the outlet tube 40 in combination with a peristaltic pump as the pump transport system therefore minimizes the interactions of the liquid 34 with other materials of construction. Suitable peristaltic pumps are sold, for example, by Simon.

A vacuum pump is an alternative embodiment of the transport system 38. If a vacuum pump is used as the transport system 38, the liquid 34 is removed from the wafer surface 36 by suction. Removing the liquid 34 by suction can volatilize either the liquid 34 or components dissolved in the liquid 34.

The nebulizer 4 is an optional portion of the apparatus. Some analyzers 6 such as an inductively coupled plasma mass spectrometer are typically coupled to the nebulizer 4. Other analyzers 6, however, may not require the nebulizer 4. In one embodiment, the nebulizer 4 is manufactured by Precision Glass. In this embodiment, the nebulizer 4 mixes argon gas with the sample liquid 34 to better retain the integrity of the droplets in the aerosol. The invention, however, is not limited to a particular type of nebulizer 4 and thus a variety of nebulizers 4 from a variety of manufactures can be used. For example, the nebulizer 4 can include quartz concentric, v-groove, plastic concentric, cross flow, high energy efficient, micro, pneumatic spray, thermospray, jet-impact, glass frit, and ultrasonic nebulizers. These are commercially available from manufactures such as Glass Expansion, Meinhardt, and Precision Glass.

The analyzer 6 can be any suitable analytical instrument for performing an analytical method. The analytical methods performed by the analyzer 6 can include, but are not limited to, X-Ray Fluorescence (XRF), Secondary Ion Mass Spectroscopy (SIMS), Ion Chromatography (IC), Inductively Coupled Plasma-Mass Spectroscopy (ICP-MS), Inductively Coupled Plasma-Optical Emissions Spectroscopy (ICP-OES), infrared analysis, chemical analysis, or other suitable spectroscopic methods. In some of the analytical methods, such as XRF or infrared spectroscopy, it is necessary to create a dry residue from the sample before performing the analysis.

Figure 4:
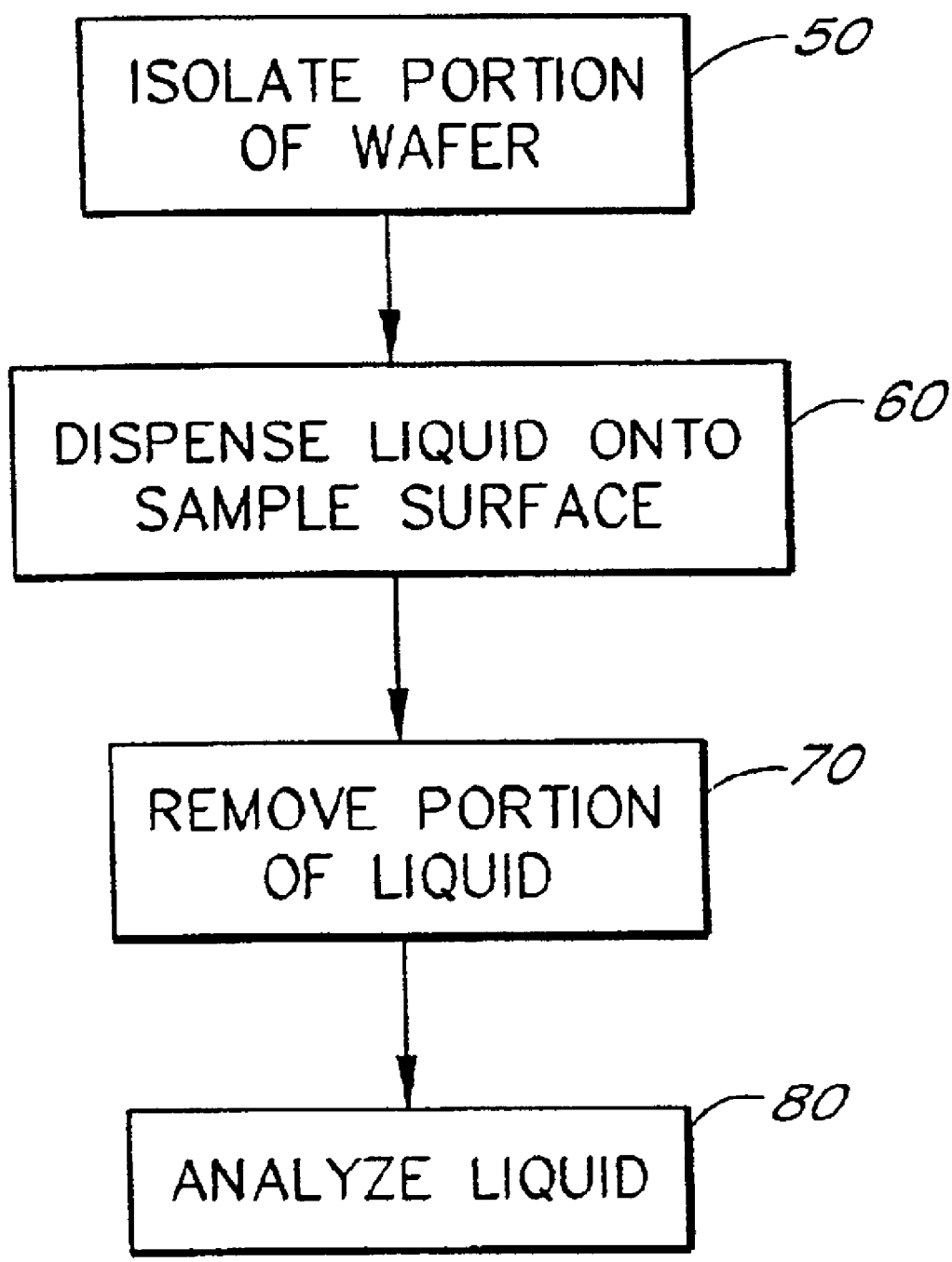
FIG. 4 is a flow chart of a manner of obtaining and analyzing a sample according to an embodiment of the invention.

FIG. 4 shows a flow chart of the invention. In block 50, a portion of the wafer 30 is isolated. In block 60, the liquid 34 is dispensed onto the wafer surface 36. In block 70, a portion of the liquid 34 is removed with the transport system 38. In block 80, the liquid 34 is analyzed in the analyzer 6. Because the liquid 34 was confined to the isolated portion of the wafer 30, the analysis of the liquid 34 is representative of the isolated portion of the wafer 30.

The following examples describe various embodiments of the manner of sampling and analyzing with the invention. The examples are not meant to be limiting to the invention but simply illustrate aspects of the invention.

A wafer 30 comprising BPSG (borophosphosilicate glass) is analyzed. In block 50, the sampling apparatus 2 is placed on the surface of the wafer 30. The base 26 forms a seal with the BPSG wafer 30 thereby isolating a portion of the wafer.

Proceeding to block 60, the sampling apparatus 2 dispenses aqueous hydrofluoric acid having a concentration of 0.1 to 5 percentage of volume is introduced into the inner tube 18 as the liquid 34. The aqueous hydrofluoric acid flows through the inner tube 18 and contacts the wafer surface 36. The aqueous hydrofluoric acid spreads across the wafer surface 36 but is confined to the area of the wafer 30 which is isolated by the inner perimeter of the outer tube 14. The aqueous hydrofluoric acid dissolves BPSG on the isolated portion of the wafer surface 36.

Proceeding to block 70, the aqueous hydrofluoric acid and dissolved BPSG build up in the outer tube 14. The peristaltic pump as the transport system 38 directs the liquid 34 and dissolved BPSG through the outlet tube 40 into the nebulizer 4. Proceeding to block 80, the nebulizer 4 mixes the aqueous hydrofluoric acid and dissolved BPSG with argon gas. The nebulizer then forwards this mixture to the analyzer 6. In this example, the analyzer 6 is an inductively coupled plasma mass spectrometer.

In another example, spatial information on the composition of the wafer 30 is obtained by moving the sampling apparatus 2 from one portion of the wafer 30 to another. Only the portion of the wafer 30 covered by the inside diameter of the sampling apparatus 2 is sampled. By moving the sampling apparatus 2 around the wafer 30 and repeating the steps of the method of FIG. 4, analyses of localized samples as a function of position on the wafer 30 are obtained.

In another example, analyses as a function of depth on the wafer 30 are obtained. In block 50, the sampling apparatus 2 is placed on a portion of the wafer 30 and a portion of the wafer 30 is isolated. Proceeding to block 60, the liquid 34 is dispensed onto the wafer 30. Proceeding to block 70, the liquid 34 is removed from the wafer surface 36 and analyzed as a function of time in block 80. The longer the sampling is performed, the greater the amount of etching. By doing analyses of the wafer 30 as a function of time and determining the rate at which the hole is formed by dissolution of the wafer 30 in the liquid 34, an analysis of the wafer 30 as a function of depth is obtained. In one embodiment, the analyses are performed by an ICP-OES. A graph of the analysis as a function of time/depth can therefore be obtained.

The invention, therefore, provides a manner of obtaining a well-defined sample from an isolated section of a wafer 30 or other soluble solid by exposing the isolated section to a liquid 34. The liquid 34 dissolves a portion of the wafer 30, a contaminant, or both. The sample or a portion of the sample is removed from the wafer 30 with a transport system 38. Using a peristaltic pump as the transport system 38 minimizes the changes in composition of the sample during the transfer. The peristaltic pump also facilitates transfer of the sample to the analyzer 6, where the sample is analyzed. Furthermore, analyses of wafers 30 and other solids can be obtained through embodiments of the invention as a function of position on the wafer and/or as a function of depth.

Although the foregoing invention has been described in terms of certain preferred embodiments, other embodiments will be apparent to those of ordinary skill in the art. Additionally, other combinations, omissions, substitutions and modification will be apparent to the skilled artisan, in view of the disclosure herein. Accordingly, the present invention is not intended to be limited by the recitation of the preferred embodiments, but is instead to be defined by reference to the appended claims.

What is claimed is:

1. A sampling apparatus for selectively evaluating portions of a wafer, the apparatus comprising:
    a first tube that is configured to isolate a portion of a semiconductor wafer;
    a second tube that is configured to dispense a liquid onto the isolated portion of the wafer;
    transfer tubing that is configured to transfer a portion of the liquid to an analyzer; and
    a peristaltic pump configured to direct the liquid in the transfer tubing to the analyzer, such that the analyzer is able to measure as a function of time an etch depth at the isolated portion of the wafer.

2. The sampling apparatus of claim 1, wherein the first tube surrounds the second tube.

3. The sampling apparatus of claim 1, wherein the liquid comprises an etchant.

4. The sampling apparatus of claim 1, wherein the transfer tubing is connected to the first tube.

5. The sampling apparatus of claim 1 further comprising a nebulizer that is in communication with the transfer tubing.

6. The sampling apparatus of claim 1, wherein the analyzer is an inductively coupled plasma-optical emissions spectrometer.

7. The sampling apparatus of claim 1, wherein the analyzer is configured to evaluate the liquid as a function of time.

8. The sampling apparatus of claim 1, wherein the analyzer is configured to evaluate the composition of the isolated portion of the wafer at different depths.

9. A test system that evaluates isolated portions of a semiconductor wafer, the testing system comprising:
    a sampling apparatus that is configured to dispense a liquid onto an isolated section of a semiconductor wafer, the sampling apparatus further comprising:
        an outer tube having an inner wall and an outer wall, the outer tube configured to form a seal between the outer tube and the isolated section of the wafer; and
        an inner tube within the outer tube, the inner tube configured to dispense a liquid within the isolated section of the wafer;
    transfer tubing comprising a first end and a second end, the first end connected to the outer wall of the outer tube, the second end connected to an analysis system, the transfer tubing further comprising a flexible outer surface wherein the transfer tubing is configured to transfer a portion of the liquid from the sampling apparatus to the analysis system; and
    a peristaltic pump in communication with a portion of the flexible outer surface of the transfer tubing, the peristaltic pump configured to direct the liquid in the transfer tubing to the analysis system.

10. The test system of claim 9, wherein the outer tube is configured to apply the liquid to the isolated section of the wafer.

11. The test system of claim 9, wherein the transfer tubing is PFTE tubing.

12. The test system of claim 9, wherein the analysis system comprises a spectrometer.

13. The test system of claim 9, wherein the analysis system comprises an inductively coupled plasma mass spectrometer.

14. The test system of claim 9, wherein the analysis system comprises a nebulizer.

15. The test system of claim 9, wherein the peristaltic pump is configured to apply successive waves to the outer surface of the transfer tubing.

16. A semiconductor testing apparatus comprising:
    a sampling apparatus that is configured to dispense a liquid onto an isolated section of a semiconductor wafer;
    transfer tubing in communication with the sampling apparatus, the transfer tubing configured to transfer a portion of the liquid from the sampling apparatus; and
    a peristaltic pump in communication with the transfer tubing, the peristaltic pump configured to direct the liquid in the transfer tubing to an analyzer the analyzer configured to measure as a function of time an etch depth at the isolated section of the wafer.

17. The semiconductor testing apparatus of claim 16, wherein the peristaltic pump does not contaminate the liquid.

18. The semiconductor testing apparatus of claim 16, wherein the liquid is an etchant.

19. The semiconductor testing apparatus of claim 16, wherein the sampling apparatus is configured to seal the isolated section of the wafer from other portions of the wafer.

20. The semiconductor testing apparatus of claim 16, wherein the transfer tubing has a flexible outer surface.

21. The semiconductor testing apparatus of claim 16, wherein the peristaltic pump applies pressure to the surface of the transfer tubing.

22. The semiconductor testing apparatus of claim 16 further comprising a nebulizer that is in communication with the transfer tubing and the analyzer.

23. A semiconductor testing apparatus comprising:
   a first means for isolating a portion of a wafer, the first means also for dispensing a liquid onto the isolated portion of the semiconductor wafer;
   second means in communication with the first means, the second means for transferring a portion of the liquid to an analysis system, the analysis system configured to measure as a function of time an etch depth at the isolated portion of the wafer; and
   peristaltic pumping means for transferring the liquid through the second means.

24. The semiconductor testing apparatus of claim 23, wherein the peristaltic pumping means peristaltically pumps the liquid through the second means.

25. The semiconductor testing apparatus of claim 23, wherein the second means is a tube.

26. The semiconductor testing apparatus of claim 23, wherein the analysis system comprises a mass spectrometer.

27. The semiconductor testing apparatus of claim 23, wherein the peristaltic pumping means does not contaminate the liquid.

* * * * *